(12) United States Patent
Arnold et al.

(10) Patent No.: US 8,021,056 B2
(45) Date of Patent: Sep. 20, 2011

(54) MICROFLUIDIC CONNECTIONS

(75) Inventors: Don W. Arnold, Livermore, CA (US);
Kenneth R. Hencken, Pleasanton, CA (US); Sammy S. Datwani, Dublin, CA (US); Patrick Pak-Ho Leung, Belmont, CA (US); Douglas R. Cyr, Livermore, CA (US); Jason E. Rehm, Alameda, CA (US)

(73) Assignee: AB Sciex, LLC, Framingham, MA (US)

( * ) Notice: Subject to any disclaimer, the term of this patent is extended or adjusted under 35 U.S.C. 154(b) by 0 days.

(21) Appl. No.: 12/874,055

(22) Filed: Sep. 1, 2010

(65) Prior Publication Data

US 2011/0018259 A1  Jan. 27, 2011

Related U.S. Application Data

(63) Continuation of application No. 10/599,591, filed as application No. PCT/US2005/011021 on Apr. 1, 2005, now Pat. No. 7,802,923.

(60) Provisional application No. 60/559,140, filed on Apr. 2, 2004.

(51) Int. Cl.
*G02B 6/36* (2006.01)
*G02B 6/38* (2006.01)

(52) U.S. Cl. ............... 385/53; 385/54; 385/46; 385/75

(58) Field of Classification Search .................. None
See application file for complete search history.

(56) References Cited

U.S. PATENT DOCUMENTS

| 5,443,890 | A | 8/1995 | Ohman |
| 5,486,430 | A | 1/1996 | Gorbell et al. |
| 6,095,697 | A | 8/2000 | Lehman et al. |
| 6,315,461 | B1 * | 11/2001 | Cairns .......................... 385/56 |
| 2002/0192701 | A1 * | 12/2002 | Adey ............................. 435/6 |
| 2004/0017981 | A1 | 1/2004 | Jovanovich et al. |

FOREIGN PATENT DOCUMENTS

DE  0141598 A  3/2003

(Continued)

OTHER PUBLICATIONS

International Search Report and Written Opinion for PCT/US05/11021 dated Oct. 17, 2005, 12 pages.

(Continued)

*Primary Examiner* — Tina Wong
(74) *Attorney, Agent, or Firm* — Sheldon Mak & Anderson

(57) ABSTRACT

A junction is made between a first microfluidic substrate (12) having an elongate component (303) protruding from it and a second microfluidic substrate (22) having a corresponding conduit (261). Each of the substrates has a pair of alignment features, for example planar orthogonal surfaces (13, 15; 23, 25) or grooves (141, 151; 241, 251) in opposite sides of the substrate. The substrates are placed on an alignment jig 6 having location features (63, 65) corresponding to the alignment features. The elongate component can be surrounded by a compressible gasket 40). The substrates are pushed towards each other so that the elongate component enters the conduit and the gasket, if any, is compressed. A fluid-tight junction results so long as the substrates are maintained in the necessary position, either by permanent means, or, if a junction which can be disassembled is needed, by maintaining pressure between the substrates. Novel apparatus and novel microfluidic assemblies, including microfluidic chips having grooves in their sides, are described.

6 Claims, 6 Drawing Sheets

FOREIGN PATENT DOCUMENTS

| | | |
|---|---|---|
| GB | 2359765 A | 9/2001 |
| JP | 2003515783 | 5/2003 |
| JP | A2004009273 | 1/2004 |
| JP | A2004009274 | 1/2004 |
| WO | WO0140837 A2 | 6/2001 |

OTHER PUBLICATIONS

English translation of JPA2004009273.
English translation of JPA2004009274.
English translation of DE0141598A.

* cited by examiner

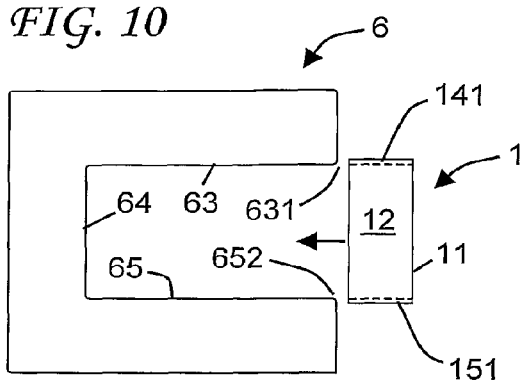
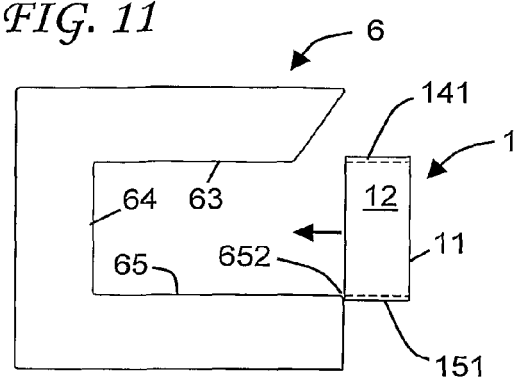
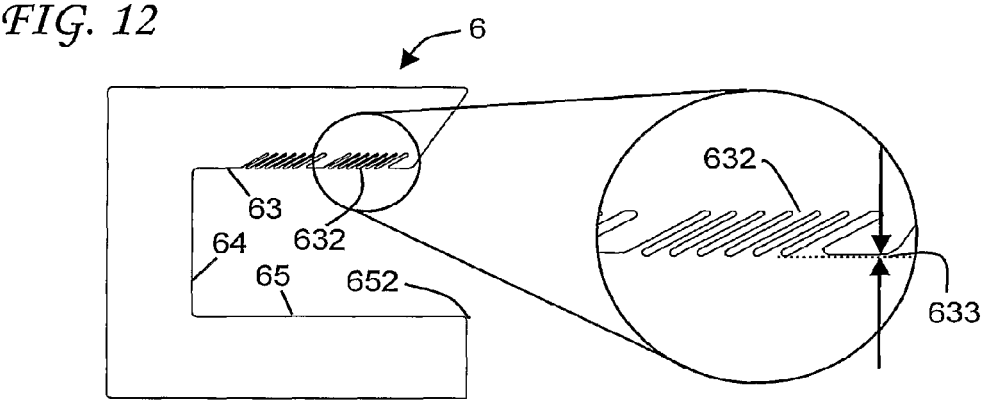
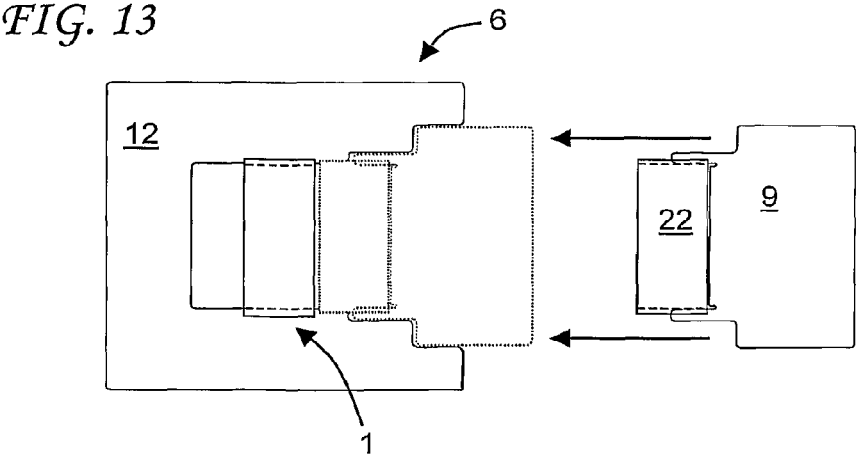

MICROFLUIDIC CONNECTIONS

CROSS-REFERENCE TO RELATED APPLICATIONS

This application is a continuation of application Ser. No. 10/599,591, filed Oct. 2, 2006, now U.S. Pat. No. 7,802,923, which is based on PCT NO. PCT/US05/11021 filed Apr. 1, 2005, which claims priority from U.S. Provisional Application No. 60/559,140 entitled Microfluidic Connector which was filed on Apr. 2, 2004, the entire disclosures of which are incorporated herein by reference for all purposes.

This application is related to (1) U.S. patent application Ser. No. 10/410,313, filed Apr. 7, 2003, (2) PCT application PCT/US 04/10234, filed Apr. 2, 2004 claiming priority from Ser. No. 10/410,313, (3) U.S. Provisional Application No. 60/559,383, filed Apr. 2, 2004, entitled Microconnector, and (4) U.S. Pat. No. 7,575,722 entitled Microfluidic Device, the entire disclosures of which are incorporated herein by reference.

STATEMENT REGARDING FEDERALLY SPONSORED RESEARCH OR DEVELOPMENT

This invention was made with United States Government support under 70NANB3H3048 awarded by the National Institute of Standards and Technology (NIST). The United States Government has certain rights in the invention.

BACKGROUND OF THE INVENTION

This invention relates to junctions in microfluidic devices.

The making of junctions comprising microfluidic conduits (for example junctions between a microfluidic conduit and a conventional elongate component, e.g. a capillary tube, optical fiber or electrical lead) presents many problems. The problems increase when a plurality of closely-spaced junctions must be made, and/or it is desirable to make a junction which can be disassembled, e.g. to remove debris or to replace disposable or modular components or parts. Known methods of making such junctions are disclosed, for example, in U.S. Pat. Nos. 6,605,472, 6,319,476, 6,620,625 and 6,832,787, U.S. Patent Application Publication Nos. US 2002/0043805 and 2003/0173781, International Publication Nos. WO/98/25065, WO/98/33001, WO 00/52376, WO 01/86155, and WO 02/070942, Sensors and Actuators B 49, 40-45 (1998) (Gonzales et al), Anal. Methods Instrum. 2 (1995) 74 (Ockvirk et al), Anal. Chem. 71, 3292 (1999) (Bings et al), Lab-on-a-Chip 1, 148-152 (2001) (Nittis et al), J. Micromech. Microeng. 11, 577 (2001) (Tsai et al), J. Micromech. Microeng. 13, 337 (2003) (Pattekar et al), and Lab-on-a-Chip 2, 42-47 (2003) (Kopf-Sill), the entire disclosures of which are incorporated herein by reference for all purposes.

SUMMARY OF THE INVENTION

We have discovered, in accordance with present invention, a simple and effective way in which junctions can be made between (i) a first substrate, preferably a microfluidic substrate, having an elongate component (e.g. an optical fiber, capillary tube, or electrical lead) protruding from it and (ii) a second substrate having a corresponding conduit, preferably a microfluidic conduit, into which the elongate component is to be placed. Further more, the invention can be used to make a junction which can be disconnected and later reconnected, to the same or different substrate; such a junction is referred to herein as a "repeatable junction".

Each of the substrates has a pair of spaced-apart alignment features. Examples of alignment features are (a) adjacent faces of the substrate at right angles to each other, (b) two grooves in opposite sides of the substrate, and (c) a groove in a face of the substrate and an adjacent face of the substrate.

One or both of the substrates can for example be (a) a single microfluidic chip which includes the alignment features, (b) a chip assembly which comprises a plurality of microfluidic chips which are bonded together one on top of the other, the alignment features being on the same or different chips, (c) a chip assembly which comprises two or more microfluidic chips which are bonded together side-by-side and/or end-to-end, the alignment features being on exposed surfaces of the chip assembly, (d) an assembly comprising a chip holder which holds (i) a single microfluidic chip or (ii) a chip assembly as defined in (b) or (c), the alignment features being on exposed surfaces of the chip holder and/or the chip or chip assembly, or (e) a chip assembly which comprises (i) a connection chip or assembly which is as defined in (a), (b), (c) or (d), and (ii) a microfluidic substrate which, for one reason or another, cannot be directly connected or is preferably not directly connected to a junction of the invention.

The substrates are positioned on an alignment jig having location features corresponding to the alignment features on the substrates (for example the location features can be two flat surfaces at right angles to each other, or two opposed flanges which fit into grooves in the substrates). One or both of the substrates is then moved relative to the other, maintaining the alignment features in contact with the location features, so that the elongate component enters the microfluidic conduit and the substrates are brought into a sealable relationship around the elongate component.

Preferably, a deformable gasket is (i) positioned around the protruding elongate component before the first substrate is positioned on the jig, or while it is positioned on the jig, and (ii) is compressed by the relative movement of the substrates to form a liquid-tight seal between the elongate component and the substrates. In this way, a repeatable junction can be made, since the junction can be liquid-tight so long as the substrates are pressed together, but can be disassembled by removing the pressure and separating the substrates. An alternative way of making the junction liquid-tight is to secure the substrates together permanently, e.g. through the use of an adhesive to secure the substrates together directly or indirectly (e.g. through a gasket, which may be deformable or substantially undeformable).

The invention includes novel junctions which can be prepared by the method of the invention described above and by other methods; novel apparatus and means for carrying out the method of the invention; novel substrates, including novel microfluidic chips, suitable for use in the method of the invention, and for other purposes; and novel methods of making such novel substrates.

In a first preferred aspect, this invention provides a junction, preferably a fluid-tight junction, comprising an elongate component which passes through the interface between two substrates, at least one of the substrates being a microfluidic substrate, and the elongate component being surrounded, at the interface, by a gasket. In a preferred embodiment, the junction is as defined in claim 1 below.

In a second preferred aspect, this invention provides a method of making a junction, preferably a liquid tight junction, which comprises providing two substrates, preferably microfluidic substrates, each of which has a pair of alignment features thereon, one having an elongate component extending from it and the other having a conduit within it; placing the substrates on an alignment jig with the alignment features in contact with the alignment jig; and sliding one or both of the substrates along the alignment jig so that the elongate component enters the conduit. In a preferred embodiment, the method is used to make a junction as defined in claim 1 by a method as defined in claim 8 below.

In a third preferred aspect, this invention provides an assembly which comprises a microfluidic substrate and which has two parallel side faces each of which includes a groove, the grooves being separated from each other by a constant distance and preferably lying in the same plane. In the simplest embodiments of this aspect of the invention, the grooves are in parallel side faces of the microfluidic substrate, and in this embodiment the assembly can consist essentially of the microfluidic substrate. More complex assemblies are described below.

When the assemblies of the third preferred aspect of the invention include a conduit which extends to a mating face which is orthogonal to the grooves, they are particularly (but not exclusively) useful in the method of the second preferred aspect of the invention. However, the assemblies (whether or not they contain such a conduit) are also useful in other contexts. The grooves facilitate handling of the substrates, e.g. through the use of chip holders, tweezers etc. having flanges which fit into the grooves, and their presence is, therefore, useful in a wide variety of situations in which a microfluidic assembly is to be positioned accurately in relation to other apparatus.

In a fourth preferred aspect, this invention provides a method of making an assembly according to the third preferred aspect of the invention in which the grooves are in the side faces of the microfluidic substrate, the method comprising
(A) providing a microfabricated composite having a plurality of groove-forming conduits which are parallel to each other and which preferably lie in the same conduit plane; and
(B) dividing the composite along (a) a plurality of groove-forming planes which are parallel to each other and each of which (i) is at right angles to the conduit plane and (ii) passes through a groove-forming conduit, and (b) a plurality of mating planes which are parallel to each other and each of which is at right angles to the conduit plane and the groove-forming planes, thus producing a plurality of said microfluidic chips.

In one embodiment, the microfabricated composite also includes a plurality of additional microfluidic conduits; the groove-forming planes do not pass through any of the additional conduits, and at least some of the mating planes pass through at least one additional conduit. The microfluidic chips produced by this embodiment are suitable for use in the method of a second preferred aspect of the invention.

In a fifth preferred aspect, this invention provides an assembly which comprises
(1) a first substrate assembly as defined in claim 8 below; and
(2) a deformable sealing gasket which surrounds the intermediate portion of the elongate component.

The assembly preferably also comprises
(3) a gasket retainer which substantially surrounds the sealing gasket and limits deformation of the gasket.

In the sixth preferred aspect, this invention provides apparatus, e.g. an alignment jig or a chip caddie, which is suitable for use in the method of the second preferred aspect of the invention and which comprises a frame and two opposed flanges which lie in the same plane and can slidably engage grooves in an assembly of the third aspect of the invention.

BRIEF DESCRIPTION OF THE DRAWINGS

The invention is illustrated by the accompanying drawings, which are diagrammatic and not to scale, in which the same reference numerals are used to denote the same or similar components, and in which FIGS. 10, 11 and 12 are top views of flange members for use in making connections, FIG. 13 is a top view showing the use of a chip caddy to make a connection.

DETAILED DESCRIPTION OF THE INVENTION

Figure 1:
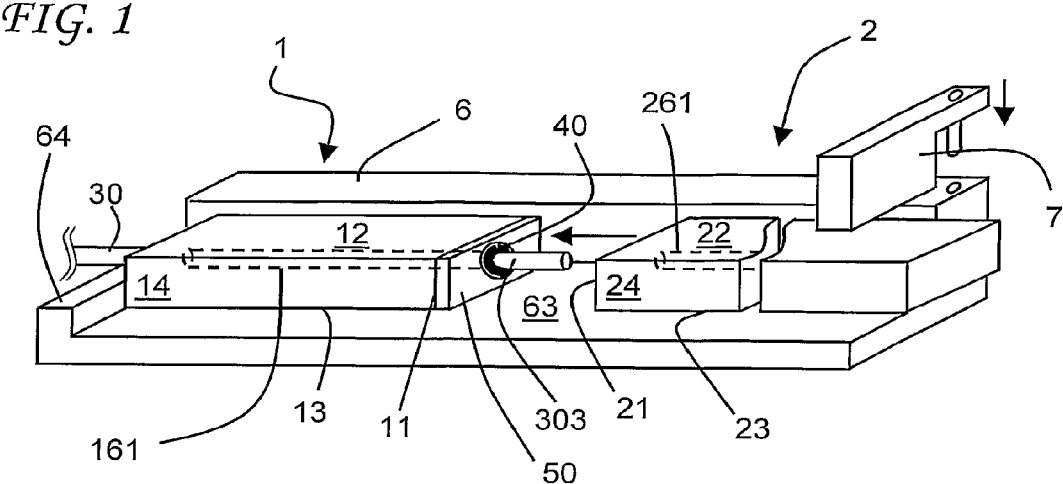
FIG. 1 is a perspective view of two substrates which are about to be connected.

In the Summary of the Invention above, the Detailed Description of the Invention, and the Claims below, and the accompanying drawings, reference is made to particular features of the invention, such features including for example aspects, components, ingredients, devices, apparatus, systems, steps and embodiments. It is to be understood that the disclosure of the invention in this specification includes all possible combinations of such particular features. For example, where a particular feature is disclosed in the context of a particular aspect, a particular embodiment, a particular Figure, or a particular claim, that feature can also be used, to the extent possible, in the context of other particular aspects, embodiments, Figures and claims, and in the invention generally. The invention claimed herein includes the use of features which are not specifically described herein but which provide functions which are the same as, equivalent to, or similar to, features specifically described herein.

The term "comprises" and grammatical equivalents thereof are used herein to mean that other features are optionally present. For example, an assembly "comprising" (or "which comprises") components A, B and C can contain only components A, B and C, or can contain not only components A, B and C but also one or more other components. Where reference is made herein to a method comprising two or more defined steps, then, unless the context requires otherwise, the defined steps can be carried out in any order or simultaneously, and the method can include one or more other steps which are carried out before any of the defined steps, between two of the defined steps, or after all the defined steps. The term "at least" followed by a number is used herein to denote the start of a range beginning with that number (which may be a range having an upper limit or no upper limit, depending on the variable being defined). For example "at least 4" means 4 or more than 4, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number. For example, "from 6 to 500" or "6-500" means a range whose lower limit is 6 and whose upper limit is 500. The numbers given herein should be construed with the latitude appropriate to their context and expression. The terms "plural" and "plurality" are used herein to mean two or more. The terms "planar face" and "planar surface" are used herein to denote a surface such that a straight line joining any two points on the surface lies wholly on the surface.

When reference is made herein to "a", "an", "one" or "the" feature, it is to be understood that, unless the context requires otherwise, there can be one or more than one such feature. For example, when reference is made herein to a feature selected from a list of features, it is to be understood that, unless the context requires otherwise, the feature can be a single one of the listed features or two or more of the listed features.

When reference is made herein to a first feature and/or a second feature, it is to be understood that unless the context requires otherwise, such terminology is used herein for convenience in identifying such features, and means that either or both features can be present, and that when both features are present, they can be the same or different.

Where reference is made herein to two or more components (or parts or portions etc.), it is to be understood that the components can be, unless the context requires otherwise, separate from each other or integral parts of a single structure or a single component acting as the two or more specified components.

The term "microfluidic conduit" is used herein to denote an elongate conduit of circular or non-circular cross-section having an equivalent diameter of at most 1.0 mm; the term includes any conduit having the specified dimensions, and is not limited to conduits through which, in use, a fluid flows. The term "equivalent diameter" is used herein to denote the diameter of a circle having the same cross-sectional area as the cross-sectional area of the conduit. The term "elongate" is used to denote a conduit having one dimension (its length) which is substantially greater than, preferably at least 4 times, e.g. at least 6 times, each of its other dimensions. The references herein to the diameter of a conduit refer to the internal equivalent diameter of the conduit, unless otherwise stated.

The term "microfluidic substrate" is used herein to denote a substrate containing a microfluidic conduit. The term "microfluidic chip" is used herein to denote a microfluidic substrate manufactured by a process which includes forming a three-dimensional pattern on a wafer and bonding the patterned face of wafer to another wafer.

The term "alignment axis", when used herein in relation to an alignment feature which is a planar surface, denotes a line which lies in the surface (and which is parallel to the conduit axis of any first end portion (FEP) or second end portion (SEP) conduit present in the substrate).

Cross-Sections of Conduit and Elongate Components

In some embodiments, each of the microfluidic conduits and each of the elongate components (if present) is substantially circular, thus defining a flow path which is substantially circular or is annular with a substantially constant width. The invention is, therefore, often described with reference to such conduits, elongate components and flow paths. It is to be understood, however, that the invention includes the use of other conduits, elongate components and flow paths. For example, one or more of the conduits and/or one or more of the elongate components can have a non-circular cross-section, for example can have a polygonal cross-section, including rectangular (including square), diamond-shaped and triangular cross-sections; for example the elongate component can be one of the commercially available optical fibers having a non-circular cross-section; and/or a component can be off-centered in a conduit. In these cases, the system will contain a flow path whose cross-section is noncircular and/or is an annulus which is irregular in width. The conduits and the elongate components in the region of the junctions will typically be of the same shape. The conduits in other parts of microfluidic devices can have, and often will have, cross-sections and/or cross-sectional areas which are different from the conduits in the region of the junctions.

Substrates

The substrates used in the present invention can be prepared in any way. However, the invention is particularly valuable when each of the substrates has been made by the method of the fourth preferred aspect of the invention. The microfabricated composite used in that method is preferably prepared by a method comprising (1) etching (or otherwise producing) a first three-dimensional pattern on a face of a first wafer;

(2) providing a second wafer, and optionally etching (or otherwise producing) a second three-dimensional pattern on a face of the second wafer, the second pattern optionally comprising a part which is substantially a mirror image of at least part of the first pattern;

(3) securing together the etched face of the first wafer and a face of the second wafer, thus forming the composite which includes the groove-forming conduits and, when desired, conduits corresponding to the FEP and SEP conduits; preferably the wafers are bonded together in a way such that the composite is a substantially monolithic body.

The wafers can be composed of any ceramic material which can be etched or otherwise treated to produce desired patterns, including for example silica, silicon, glass, quartz and alumina. The wafers can also be made by other techniques, e.g. by shaping a polymeric material using microfabricated embossing molds, microinjection molding, or soft lithography methods.

The composite can comprise two or more wafers bonded together on top of each other. When there are three or more wafers, the junctions between each pair of wafers can provide the same or different conduit systems. For example, the conduit system between one or more of the pairs of wafers can provide conduits corresponding to FEP and/or SEP conduits. The thicknesses of the wafers can be the same or different. The composite can comprise vias which join patterns between different pairs of wafers. The patterns can be, but need not be, adjacent patterns. Alternatively or additionally, one or more connections between different patterns can be made by conduits which extend to a mating face and auxiliary conduits in one or more auxiliary substrates connected (preferably by a junction according to the first preferred aspect of the invention) to the mating face.

The composite, and the chips obtained from the composite, may for example have a thickness of 0.5 to 5 mm, e.g. 0.5 to 2 mm. A plurality of such chips can be bonded together one on top of the other and/or side-by-side. One or more junctions of the invention can be made to one or more of the chips. One or more such chips can be bonded together with one or more chips which do not have grooves in the side faces.

The etched features on one or both wafers can be of any cross-section, e.g. half round, V-shaped, or rectangular (including square), and can result in conduits of the same cross-section (if the contacting surface of the other wafer is not etched) or, if the contacting surface of the other wafer is also etched (either as a mirror image or in a different shape) a cross-section which combines the cross-sections of the two etched features. The sections which are to become the entrance(s) to the FEP and/or SEP conduit(s) can be enlarged and tapered to facilitate entrance of an elongate component.

In some embodiments, the etched pattern repeats a pattern corresponding to the first substrate and an adjacent second substrate, so that the division of the composite along the mating planes produces both FEP and SEP mating faces. As a theoretical ideal, the first and second substrates which were adjacent to each other in the composite are reassembled at the junction. In practice, however, it is difficult to achieve this ideal. In other embodiments of this method, all the first substrates are produced from a first composite and all the second substrates are produced from a second composite.

The number of substrates produced from each composite can be for example from 6 to 500, or even higher, depending on the sizes of the composite and the substrates. Substrates produced by this method are referred to herein as "microfluidic chips", this term being used to include those substrates in which no liquid flows through the etched conduit(s) when the substrate is in use, for example a substrate in which the or each conduit accommodates an elongate element.

The groove-forming conduits can for example have an equivalent diameter of 70 to 500 µm, preferably 120 to 300 µm; and preferably have a symmetrical shape and size chosen having regard to the method of division, e.g. having regard to the thickness of a blade use to dice the composite, which is typically 100 to 250 µm. For example, the groove-forming conduits can have width of 200 to 500 µm and a height of 50 to 400 µm. A preferred shape for the groove-forming conduits is a rectangle with rounded corners and having its major axis in the plane of the composite.

The distance between the inner boundaries of the grooves is fixed by the patterns etched into the composite, which can be very precisely controlled, and which remains the same even if the line of division does not precisely follow the center of the groove-forming conduit. This reduces the likelihood that misalignment will be caused by irregularity of the faces of the substrates and/or of the planar surfaces which they contact, and/or by division of the composites along lines which are not in exactly the same relationship to the features etched into the composite.

When the elongate component is a capillary tube from which a liquid flows into the SEP conduit, and the liquid is free from any particles deliberately dispersed therein, the second conduit can include a weir near the end of the capillary tube, so that any particles which are accidentally entrained by the liquid are retained on the weir. The weir can be part of the etched pattern(s).

Elongate Components

There can be a single elongate component secured within a single FEP conduit and entering a single SEP conduit, or a plurality (e.g. 3 to 7) elongate components secured within a corresponding plurality of FEP conduits and entering a corresponding plurality of SEP conduits (not all of which, however, need be microfluidic conduits). When there is a plurality of elongate components, they may be separated from each other, at the mating face, by, for example, a distance of 0.25 mm or more. When there is a plurality of elongate components, the elongate components may be combined together as a ribbon cable. In this case, the individual components can be separated from each other before being secured within separate FEP conduits, or the FEP conduit can be shaped so that the entire cable lies within it. In the latter case, the elongate components extending from the FEP mating face are separated from the rest of the ribbon cable and are inserted into separate SEP conduits.

Generally, there will be at least one elongate component which is an active component, the term "active component" being used herein to denote a component which will play a part in the later operation of a device (i.e. after the junction comprising the active component has been created). When there is a plurality of elongate components, one or more (including all) of them can be active components. Examples are such active components include capillary tubes through which liquids are introduced into the device; arms which enter a second conduit and modify the flow of a liquid through the second conduit during operation of the device; optical fibers by means of which a liquid flowing through the device is illuminated and/or observed (and which may also modify the flow of a liquid); and electrical leads. Alternatively, some of the elongate components (e.g. all but one of them) can be passive components, i.e. components which are not active components, but have some other function, e.g. to serve as locating members as the substrates are pushed together to create the junction. Such passive components need not enter microfluidic conduits and need not be surrounded by a sealing gasket. However, they can enter microfluidic conduits and/or be surrounded by a sealing gasket, for example to ensure a substantially uniform pressure between the mating faces of the substrates.

The elongate component can for example have an equivalent diameter of 25 to 900 micrometers, e.g. 100 to 400 micrometers. The length of the fixed portion secured within the FEP conduit may be for example 0.1 to 10 mm, and there can be a substantially longer remote portion extending within and/or beyond the first substrate away from the junction. The remote portion can be connected to another microfluidic device or to conventional equipment. The remote portion can be curved, e.g. through an angle of 180°, and include an opposite end which enters another SEP conduit, to provide communication between different microfluidic systems or between different parts of the same microfluidic system. The length of the intermediate portion surrounded by the gasket can be for example 0.05 to 0.2 mm in the sealed junction (i.e. the thickness of the gasket in its deformed sealing configuration), and 0.075 to 0.3 mm before compression of the gasket (i.e. the thickness of the uncompressed gasket). The length of the free portion can be for example 0.1 to 2 mm before compression of the gasket. The length of the free portion can, if desired, be set precisely and reproducibly by placing the first mating faces against a measurement substrate having a measurement conduit of desired depth, and pushing the elongate component through the first conduit until it contacts the bottom of measurement conduit, and then securing the elongate element in the first conduit, e.g. with an adhesive and/or a clamp.

It is also possible for the second substrate to include one or more additional conduits each of which extends to the second mating face and has secured therein an elongate component which extends from the second mating face and enters a corresponding conduit in the first substrate.

When the elongate component is an optical fiber, the SEP conduit may contain a second optical fiber, so that the ends of two optical fibers are positioned close to or in contact with each other at the junction.

Bottom and Side Faces as Alignment Features

In one embodiment of the invention, the alignment features are the bottom face and one of the side faces of each substrate, and the jig location features are orthogonal planar surfaces which are contacted, during the making of the junction, by the bottom and side surfaces respectively. A potential disadvantage of this embodiment is that, even when the mating faces are precise mirror images of each other, the ease of making the junction can be adversely affected by any irregularity (e.g. caused by contamination) of any of the contacting surfaces. Similar difficulties will be produced by any difference in the distance of the FEP and SEP conduits from the bottom and side surfaces. Such variation in distance will not occur when the two substrates were adjacent to each other in a microfabricated composite which was divided to produce the two substrates, the division producing the two mating surfaces; and it is unlikely to occur when both substrates result from division of a single microfabricated composite. It can, however, occur when the substrates result from division of different microfabricated composites, even when the different composites have been prepared and divided by procedures which are intended to be identical. When a number of composites are made using the same pattern(s) to etch the composites, it is not difficult to ensure that the etched patterns are, for the purposes of the present invention, identical. However, there can be a failure to divide the different composites along lines which are in exactly the same relationship to the pattern. Such failure results in substrates having conduits which are not placed in exactly the same relationship to the faces of the substrate.

Alignment Jigs with Planar Jig Location Features

Alignment jigs with planar orthogonal surfaces as the jig location features can be made in any convenient way. The jig preferably includes a stop against which one of the substrates can bear while the other substrate is slid towards it to create the junction. The jig can include means, for example resiliently deformable means, for urging one or both of the faces serving as the alignment features against the corresponding surfaces of the jig serving as the location features.

Grooves as Alignment Features

Another embodiment of the invention mitigates the difficulties which can arise when the faces of the substrates are used as the alignment features. In this embodiment, the alignment features are grooves in the side faces of each substrate assembly. Such grooves can conveniently be created as a part of the process which also produces the microfluidic features of the substrate, as described above.

Alignment Jigs with Flanges

When the alignment features are grooves in the side faces of the substrates, the jig location features are flanges which are separated from each other by a constant distance, and have thin edge portions which fit slidably into the grooves, and which generally lie in the same plane. The thickness of the edge portions should be somewhat less than, e.g. 10 to 30 micrometers less than, the height of the groove. The distance between the flanges should be slightly greater than, for example 20-40 micrometers greater than, the distance between the grooves. The flanges can be of uniform thickness, or can have relatively thin edge portions and relatively thick body portions to make the flanges more rigid. It is preferable, particularly if the flanges are of uniform thickness, for the flanges to be mounted to a rigid base, for example between two rigid base members, to minimize flexing of the edge portions out of the plane during use. One or both of the flanges can have a tapered end portion, e.g. a rounded corner, to help the substrate to enter the gap between the flanges. One or both of the flanges can be substantially shorter than the other, so that at least part, e.g. 50-100%, of one groove of the substrate can be fitted over the longer flange, and the other groove thereafter fitted over the shorter flange as the substrate is pushed between the flanges.

The alignment jig can include means for urging one or both of the flanges towards the center of the substrate, in order to ensure that the flanges enter into the grooves as far as is consistent with the need to slide the substrates relative to each other. For example, the edge portion on one or both of the flanges can comprise a section which is resiliently deformable in the plane of the flange. The resiliently deformable section can for example include a plurality of fingers with rounded ends set at an angle, preferably an acute angle, to the axis of the flange which decreases as the substrate is pushed into place between the flanges.

In one embodiment, there are two separate flanges mounted to a rigid base. This has the advantage that the separation of the flanges can be changed (by changing the relative locations at which the flanges are mounted to the base), but the disadvantage that the separation may change accidentally during use.

In another embodiment, the two flanges are the legs of a monolithic, planar, generally U-shaped flange member. This ensures that the distance between the flanges does not change accidentally during use.

The flanges are preferably composed of a metal, particularly an alloy metal, or other rigid material which can be fabricated with a high degree of dimensional accuracy. Suitable fabrication methods include conventional machining, laser machining, and chemical etching. Photochemical etching is particularly preferred because very good dimensional tolerances can be achieved, and because it does not induce the mechanical and/or thermal stresses which can be induced by conventional machining and laser machining.

Chip Caddies

The substrates, particularly when they are microfluidic chips, are often small and quite difficult to handle. It may be desirable, therefore, while creating or disassembling the junction, to hold one or both of the substrates in a carrier which can be more easily handled and which does not interfere with the desired operations. Such carriers are referred to herein as chip caddies. Particularly useful chip caddies are generally U-shaped bodies having legs which fit into the grooves of a substrate having grooves in its side faces and which have a length such that when the substrate is fully engaged by the caddy (i.e. the face of the substrate opposite the mating face is pressed against the base of the U), a substantial proportion of each of the grooves remains exposed. Such a chip caddy can be used in conjunction with an alignment jig having generally U-shaped flange member as described above, preferably one having legs whose ends are shaped to accommodate the chip caddy as the exposed portions of the grooves of the substrate, carried by the caddy, are pushed between the flanges. The caddy can optionally be left in place after the junction has been created.

Gaskets and Gasket Retainers

When the junction is a repeatable junction, and optionally when it is a permanent junction, the intermediate portion of the elongate component is surrounded by gasket which is compressed between the first and second mating faces and is thus forced into a deformed configuration in which it forms a liquid-tight seal between the elongate component and the first and second mating surfaces. In some embodiments, the gasket is at least partially surrounded by gasket retainer which limits deformation of the gasket.

The gasket can be composed of any material which will provide the desired sealing. If the gasket is exposed to liquids passing through the second conduit during use of the junction, the gasket should be composed of a material which will not be damaged by that liquid. Particularly if the gasket is to be reused, it is preferably elastomeric with a Shore A Durometer Hardness of 40 to 100, preferably 60 to 80. Suitable materials of this kind include polymeric compositions comprising elastomers such as fluoroelastomers (e.g. by Vitons), silicones and fluorosilicones. For high-pressure operation, the gasket material preferably has high tensile strength, e.g. a tensile strength of at least 5 MPa, e.g. 10 to 50 MPa. Suitable materials of this kind, which may have little or no elasticity, include polymeric compositions based on polymer such as polyolefins (e.g. polyethylene and polypropylene), partially and fully fluorinated polyolefins (e.g. polytetrafluoroethylene), copolymers of tetrafluoroethylene and at least one other monomer, e.g. perfluoro vinyl ether), polyetherether ketones, and polyacetals [e.g. Delrin). These gaskets may have a hardness on the Shore A scale from 70 to 100 or on the Shore D scale from 30 to 80. Graphite and soft metals (e.g. copper, lead or indium) can also be used as gasket materials. The gaskets, whether reusable or disposable, can be made in any way, including injection molding, compression molding, punching, laser machining, conventional machining and micromachining. They can also be made by curing (e.g. by photopolymerization and/or by heat) suitable precursors (e.g. a room-temperature vulcanizable silicone or a mixture of perfluoropolyetheracrylate monomers containing a photoinitiator and a suitable solvent) in a mold, for example a mold which subsequently provides a gasket retainer. The gasket can be shaped or include features which localize the applied compression force in order to optimize the sealing. When there is a plurality of elongate components each of the components can be surrounded by a single gasket, or two or more of the components can be surrounded by gasket having a plurality of holes through it.

The gasket retainer, if used, provides mechanical support for the gasket while the junction is being created, and subsequently during the use of the junction, particularly at high pressures. A single gasket retainer can surround a plurality of gaskets. The gasket retainer can be composed of any material, e.g. a metal, polymer or ceramic, which will provide such support. The gasket retainer can be made in any way, including machining, chemical etching, micro machining, punching, laser machining, water jet machining, bead blasting, injection molding or compression molding. A gasket retainer and one or more gaskets surrounded by the gasket retainer can form a single article. The gasket(s) can be preformed and then secured to the retainer; or the combined article can be made by compression forming two materials simultaneously; or the gasket can be formed in situ in recesses on one or both sides of the retainer. Formation of the gasket in situ can for example be effected by injection molding, vulcanization or photopolymerization of a precursor for the gasket material. Formation of the gasket in situ can be carried out in the absence of the substrate and elongate element, or after the gasket retainer has been positioned on the first mating face with the elongate element passing through it so that the gasket material is in intimate contact with the elongate element as well as the gasket retainer.

Retaining the Seal Between the Substrates

During use of microfluidic devices including junctions of the invention, the substrates are usually maintained in relative positions such that a fluid-tight seal between them is retained. This can be done in any way. The retention can be substantially permanent, or can be releasable, so that the substrates can be separated from each other, for example for cleaning and/or replacement of one of the substrates.

Releasable retention can be achieved in any way, for example through the use of releasable mechanical retainers. In some embodiments, the retainer(s) engage(s) both substrates. In some embodiments, at least one of the substrates is restrained by a restraining body (which may be the alignment jig or a chip caddy as described below) and the retention is provided by the restraining body itself and/or by one or more retainers which engage a restraining body and one or both substrates, all which engage first and second restraining bodies which restraining the first and second substrates respectively. The retainers can cooperate with the boundaries of substrates and/or restraining bodies, and/or with features, e.g. grooves or holes, formed for this purpose in one or both substrates and/or the restraining body or bodies. The retainers can be elastically deformed so that they do not contact the substrates while the junction is being made, but snap into a retaining configuration when the fluid-tight seal has been achieved. Alternatively or additionally, the retainers can be secured in place by screws or any other form of releasable fastener. In some embodiments, the alignment jig includes one or more releasable mechanical retainers which can be secured in place, after the liquid-tight junction has been formed.

Permanent retention can for example be achieved by mechanical retainers and/or through the use of adhesives. The adhesive can for example be (i) an adhesive which joins the mating surfaces directly to each other, the adhesive being a gap-filling adhesive when a sealing gasket is used; (ii) an adhesive applied to each side of a gasket retainer surrounding a sealing gasket or to each side of an auxiliary gasket which surrounds a sealing gasket (and gasket retainer, if present) and which may be compressible or incompressible, or (iii) an adhesive applied to an elongate component. In the last case, the adhesive is preferably applied to an elongate component which does not play a part in the functioning of the device, so that it does not matter how the adhesive is distributed within the conduit receiving the elongate component.

Annular Volumes Between the Elongate Component and the Microfluidic Conduit

The clearance between the elongate component and the SEP conduit must be sufficient to permit the elongate component to enter the conduit. As a result, there is a volume of annular cross section (defined by the outside of the elongate component and the inside of the SEP conduit) between the liquid-tight seal and the end of the elongate component. Under some circumstances, this annular volume can be a dead volume which has adverse effects. The corresponding to U.S. Provisional Patent Application No. 60/559,140 and corresponding to U.S. Pat. No. 7,575,722, incorporated by reference herein, describe how these adverse effects can be reduced by providing a drain conduit from the dead volume.

Devices

Junctions according to the invention can be used in a wide variety of microfluidic devices. The fluid flowing through the microfluidic device can be of any kind, and may for example be a gas or a liquid (the term "liquid" being used to include emulsions and gels), particularly liquids having analytes dissolved therein or having particles comprising analytes dispersed therein. Devices of particular interest are the devices for examining liquid samples which are described in the PCT applications incorporated by reference herein.

In one embodiment, the invention is used to make connections to a microfluidic substrate which, for one reason or another, cannot be directly connected, or is preferably not directly connected, to a junction of the invention. Such a substrate is referred to herein as a "non-linking substrate". Examples of non-linking substrates are substrates which lack alignment features and/or which are damaged or deform when the connection is made directly to them and/or by pressures exerted on the substrate to maintain the junction. In this embodiment, one or both of the first and second substrates comprises (a) a non-linking substrate,
(b) a microfluidic substrate which can be directly connected to a junction of the invention, and
(c) one or more microfluidic conduits which make one or more connections between the substrates (a) and (b).

Often, the assembly will comprise two substrates (b) and two sets of microfluidic conduits (c), connected to respective ends of the substrate (a). More than one substrate (a) can be connected to a single substrate (b). More than one substrate (b) can be connected to a single substrate (a). The microfluidic conduits (c) can for example be capillary tubes and can lie partially or wholly within the substrate (b). If they lie partially with the substrate (b), they include intermediate portions which can be straight or curved, and which can be flexible. If they lie wholly within the substrate (b), the ends of the substrates (a) and (b) can be directly bonded to each other, for example through a glued interface and/or by other physical means, for example by potting with a suitable polymeric material.

In another embodiment, three or more substrates, e.g. 3-6 substrates, can be connected in series, with one or more of the junctions being junctions of the invention, preferably repeatable junctions, so that one or more of the substrates can easily be removed and replaced. This is particularly useful, for example, when a series of substrates connected in series comprises a filter chip which is connected by repeatable junctions and, later in the series an analysis chip. The filter chip can then easily be removed, cleaned and replaced (or removed and replaced by a new filter chip).

Drawings

Figure 2:
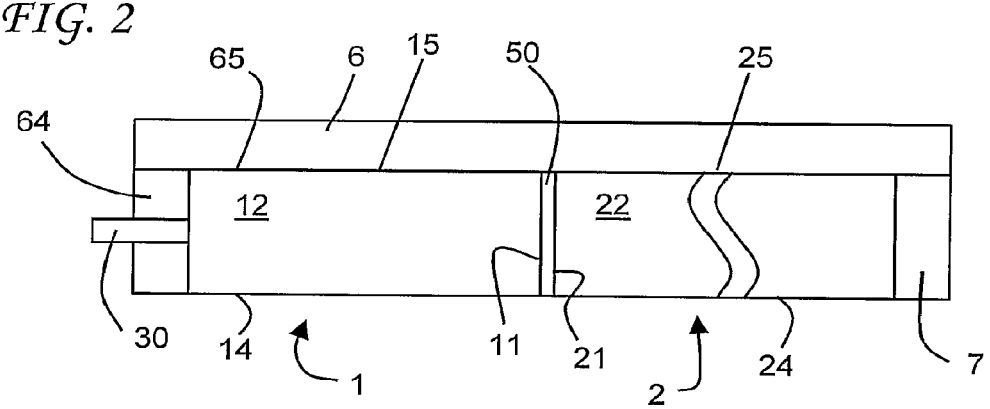
FIGS. 2 and 3 are top and cross-sectional views of the connection formed by the substrates in FIG. 1, FIGS. 4 and 5 of perspective and top views of substrates which are about to be connected.
Figure 3:
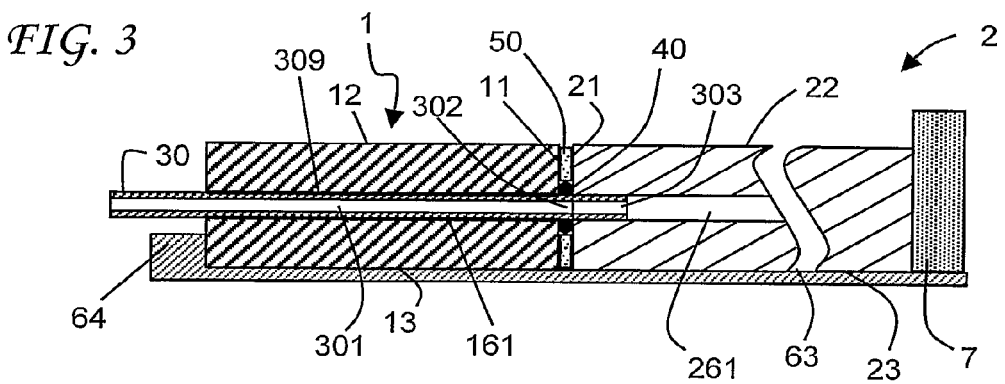

In each of FIGS. 1-3, a first substrate 1 is a rectangular parallelepiped having a planar first mating surface 11, a planar first top face 12, a planar first bottom face 13, planar side faces 14 and 15, and a first conduit 161 running through the substrate and terminating at the mating surface 11; a second substrate 2 is a rectangular parallelepiped having a planar second mating surface 21, a planar second top face 22, a planar second bottom face 23, planar side faces 24 and 25, and a second conduit 261 which extends to the mating surface 21 and is part of a microfluidic system which is not shown. The first and second conduits have the same diameter and are spaced from bottom faces 11 and 21 by the same distance and from side faces 15 and 25 by the same distance. The two substrates can for example be the product of dividing a microfabricated chip along a plane which produces the mating faces. An elongate component 30 runs through the first conduit 161, and has a fixed portion 301 secured within the first conduit 161 by an adhesive 309, an intermediate portion 302 adjacent to the first mating face 11, and a free portion 303 extending away from the mating face 11 and the intermediate portion 302. A sealing gasket 40 surrounds the intermediate portion 32 of the elongate component and is itself surrounded by gasket retainer 50. In FIG. 1, the first and second substrates are placed on an alignment jig 6 having a planar horizontal surface 63 having a stop 64 at one end, and a planar vertical surface 65. The horizontal surface 63 provides one of the jig location features of the vertical surface 65 provides the other jig location features. The first substrate is placed on the alignment jig 6 with its bottom surface 13 against the horizontal surface 63, its side face 15 against the vertical face 65, and with the end opposite the mating face against the stop 64. As shown in FIG. 1, the second substrate is placed on the alignment jig with its bottom face 23 against the horizontal surface 63, its side face 25 against the vertical surface 65 and its mating face 21 opposite to and spaced-apart from the first mating face 11. The second substrate is then pushed along the alignment jig towards the first substrate, maintaining the faces 13 and 23 against the surface 63, and the faces 15 and 25 against the vertical surface 65, so that the free portion 303 of the elongate component 30 enters the conduit 261, and the gasket 40 is compressed to provide a seal between the mating surfaces 11 and 21, with the extent of the radial deformation of the gasket 40 being limited by the gasket retainer 50, as shown in plan view in FIG. 2 and in cross-sectional side view in FIG. 3. Also shown in FIGS. 1-3 is releasable retainer 7 which can be locked in place (by locking means not shown) after the substrates have been pushed together, so that the substrates are retained in relative positions which maintain the gasket in the deformed sealing configuration.

Figure 4:
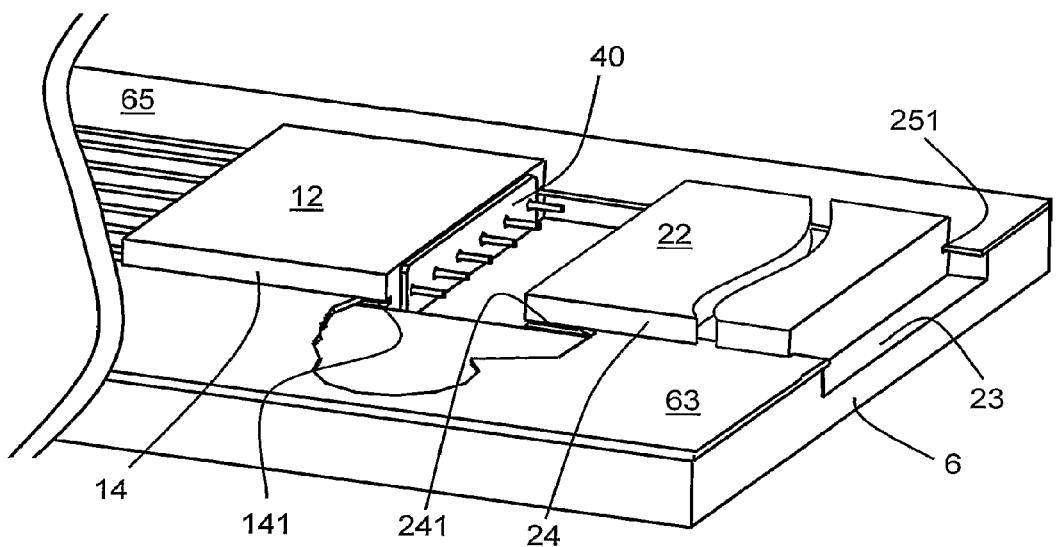
Figure 5:
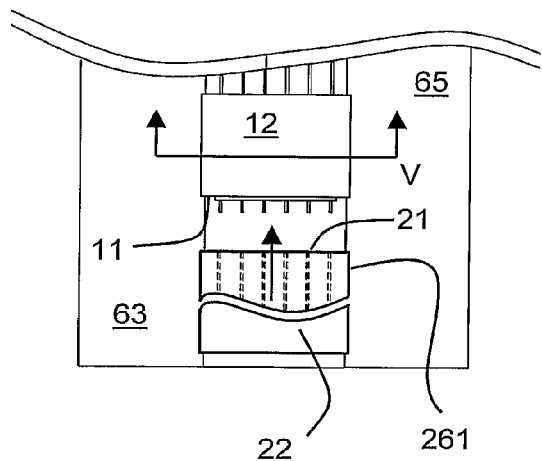
Figure 6:
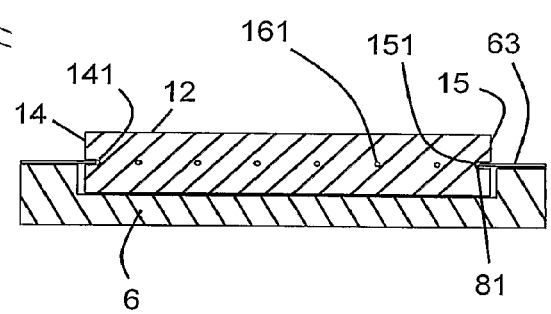
FIG. 6 is a cross-sectional view on line V of FIG. 5, FIGS. 7 and 8 are cross-sectional views of devices incorporating connections of the invention.

In each of FIGS. 4-6, a first substrate 1 is a rectangular parallelepiped having a planar first mating surface 11, a planar first top face 12, a planar first bottom face 13, planar side faces 14 and 15 having respective parallel longitudinal grooves 141 and 151 therein, and six parallel first conduits running longitudinally through the substrate, the grooves and the conduits lying in a plane parallel to the top and bottom faces, and the conduits terminating at the mating surface 11; a second substrate 2 is a rectangular parallelepiped having a planar second mating surface 21, a planar second top face 22, a planar second bottom face 23, planar side faces 24 and 25 having respective parallel longitudinal grooves 241 and 251 therein, and six parallel second conduits 261 running longitudinally through the substrate, the grooves and the second conduits lying in the same plane as the first conduits, and the conduits terminating at the mating surface 21. The first and second conduits have the same diameter and are spaced from the grooves in the side faces 15 and 25 by the same distance. The two substrates can for example be the product of dividing a microfabricated chip along a plane which produces the mating faces. Elongate components 30 run through the first conduits 161, and have fixed portions secured within the first conduits by adhesive, intermediate portions adjacent to the first mating face 11, and free portions extending away from the mating face 11 and the intermediate portions. A sealing gasket 40 surrounds the intermediate portions of the elongate components. The first and second substrates are placed in an alignment jig 6 which carries parallel flanges 63 and 65 which lie in the same plane as the grooves and the conduits, and which are spaced apart so that they fit snugly and slidably into the grooves in the side faces of substrates. The flanges thus provide the jig location features. The substrates are then pushed towards each other so that the free portions of the elongate components enter the second conduits 261, and the gasket 40 is compressed to provide a seal between the mating surfaces 11 and 21.

Figure 7:
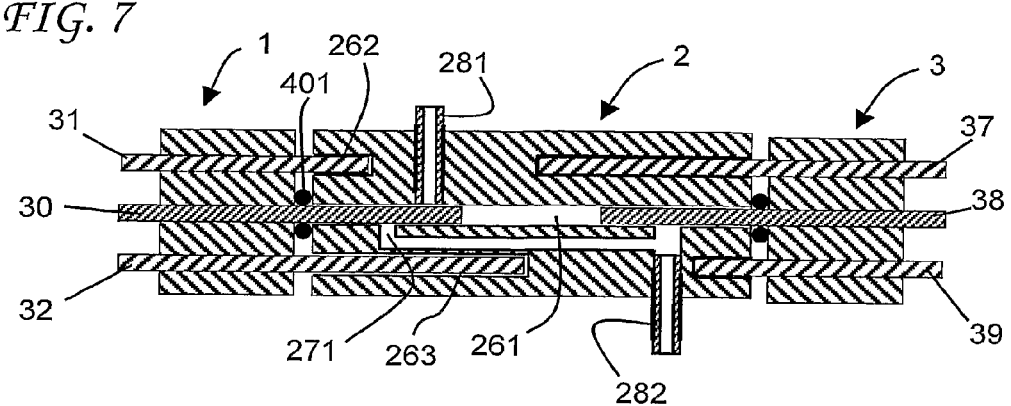

FIG. 7 shows a device comprising a substrate 2 having one end connected, through a junction of the invention, to a substrate 1, and the other end connected, through a junction of the invention, to a substrate 3. Element 30, an optical fiber, is secured within substrate 1, enters one end of microfluidic conduit 261 in substrate 2, and is surrounded by gasket 401 at the junction between the two substrates. Elements 31 and 32 are passive locating elements which enter blind conduits 262 and 263 in substrate 2. Element 32 is longer than the other elements, and, when the junction is being made, enters the conduit 263 before the other elements, thus helping to ensure satisfactory creation of the junction. The substrate 3, elongate elements 37, 38 and 39 and gasket 402 similarly provide a junction of the invention between the other end of the substrate 2 and the substrate 3. At each end of the conduit 261 the free portion of the optical fiber forms, with the conduit 261, an annular volume. Inlet 281 and outlet 282 communicate with respective inner end sections of this annular volume so that an analytical sample or other liquid entering through the inlet 281 passes successively through an annular entrance passageway, the unobstructed central portion of the conduit 261, and an annular exit passageway, before exiting through the outlet 282. The optical fibers 32 and 38 can be used to supply light to, and/or to inspect the liquid in the conduit 261. Drain conduit 271 is connected to the outer end section of the annular volume at the entrance end of the conduit 261, and thus prevents it from acting as a dead volume which would have an adverse effect on analysis of an analytical sample passing through the device, as more fully described and claimed in copending commonly assigned Provisional Application No. 60/559,383 and the copending commonly assigned application filed contemporaneously with this application by Arnold and entitled Microfluidic Device, which is now U.S. Pat. No. 7,575,722, both incorporated by reference herein. Drain conduit 271 is connected to outlet 282

Figure 8:
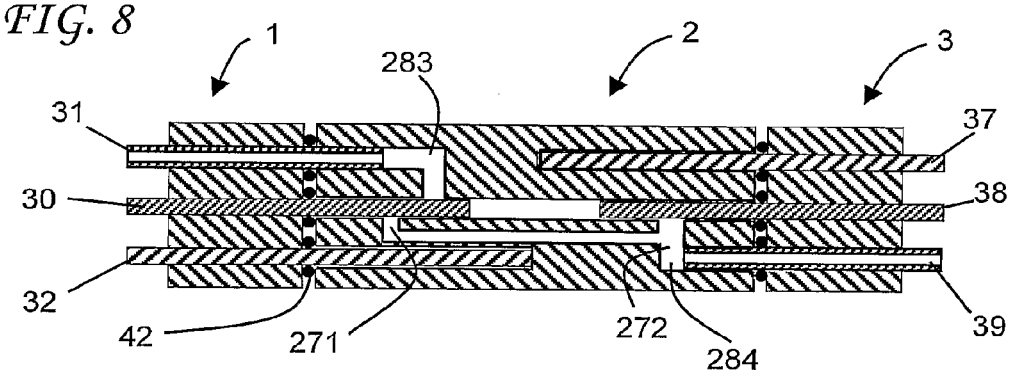

FIG. 8 shows a device which is similar to that shown in FIG. 7 except that the elements 31 and 39 are capillary tubes which enter additional microfluidic conduits 283 and 284, thus replacing the inlet 281 and the outlet 282. Gasket seal the capillary tubes 31 and 39 and are also placed around the passive elements 32 and 37.

Figure 9:
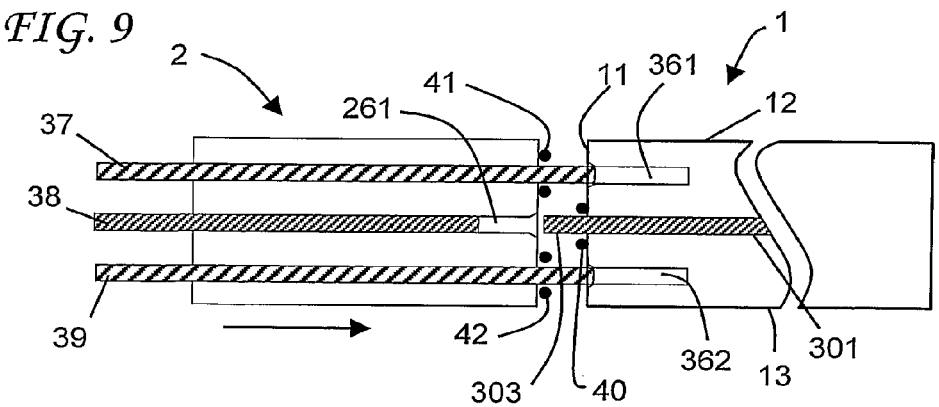
FIG. 9 is a cross-sectional view of two substrates which are about to be connected.

FIG. 9 shows a junction between a first substrate 1 and a second substrate 2. Optical fiber 303 is secured within and extends from substrate 1 into conduit 261 in the second substrate 2. Secured within the conduit 261 is a second optical fiber whose end, in the finished junction, contacts or is adjacent to the end of optical fiber 303. Passive elongate elements 37 and 39 are secured within and extend from the second substrate 2 into blind conduits 361 and 362 in the first substrate 1. Gaskets 40, 41 and 42 surround the optical fiber and the passive elements. The entrance to each of the conduits is tapered to facilitate entry of the elongate elements. The passive elements extend from the second substrate a little further than the optical fiber extends from the first substrate. They, therefore, enter the conduits 361 and 362 before the optical fiber enters the conduit 261, thus ensuring that the optical fiber is accurately located opposite the conduit 261 and reducing the risk that the optical fiber will be damaged during the creation of the junction.

FIG. 10 shows a generally U-shaped flange member 6. The base 64 of the flange member acts as a stop for a first substrate 1 which is to be inserted between the flanges 63 and 65 formed by the legs of the U-shaped member. Each of the flanges 63 and 65 has a rounded corner 631 and 652 to help the fitting of the grooves 141 and 151 of the substrate 1 over the flanges 63 and 65.

FIG. 11 is similar to FIG. 10, except that the flange 63 is shorter than the flange 65.

FIG. 12 is similar to FIG. 11, except that the flange 63 comprises a plurality of inwardly slanting fingers 632 which are elastically deformable in the plane of the flange. The fingers, when not deformed, extend inwards so that the distance between the tips of the fingers and the flange 65 is substantially the same as the distance between the grooves on the substrate. The distance between the fixed portion of the flange 63 and flange 65 is slightly greater than, for example 10 to 15 micrometers greater than, the distance between the grooves on the substrate, as shown by reference numeral 633. The first substrate is first fitted over the flange 65 and then pushed down the U-shaped member until it engages the base 64. The fingers 632 deform outwards slightly, and thus ensure that the flanges enter the grooves so far as is consistent with the need to slide the substrate. The same procedure is followed with the second substrate, thus creating the junction.

FIG. 13 shows the use of a chip caddy 9 to insert a second-loaded substrate 22 into a U-shaped flange member 6 into which a first-loaded substrate 1 has already been loaded. The ends of the legs of the flange member are shaped to accommodate the chip caddy and allow the second-loaded substrate to be pushed against the first-loaded substrate, thus creating the junction.

Figure 14:
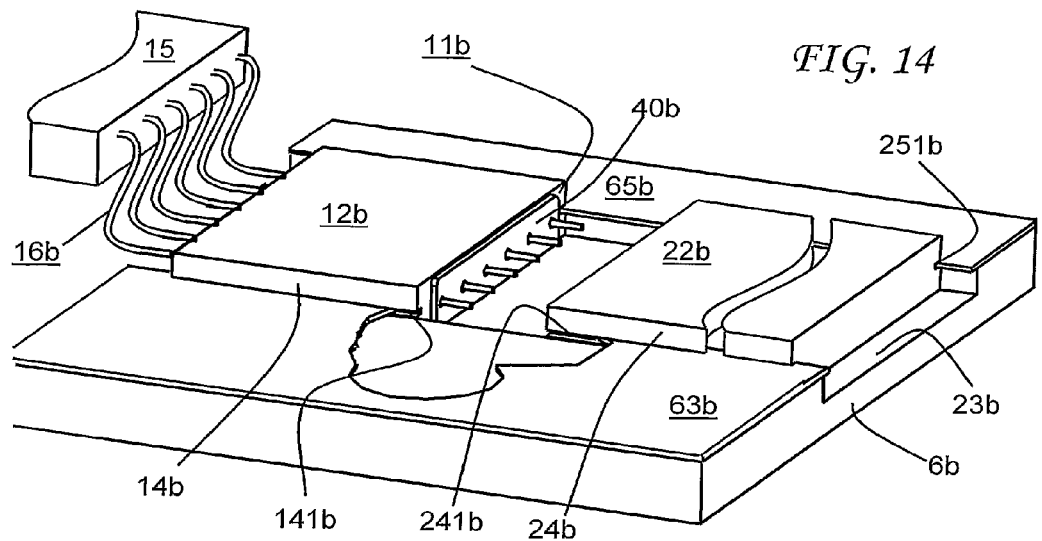
FIGS. 14 and 15 are perspective and top views of the use of the invention to make connections to a microfluidic chip which, on its own, lacks the features needed for it to be connected by the method of the invention, or which is liable to be damaged during such connection, FIGS. 16 and 17 one top and side views of a chip assembly which makes it possible to use the method of the invention to make connections to a microfluidic chip which lacks the features needed for it to be connected by the method of the invention, or which is liable to be damaged during such connection.
Figure 15:
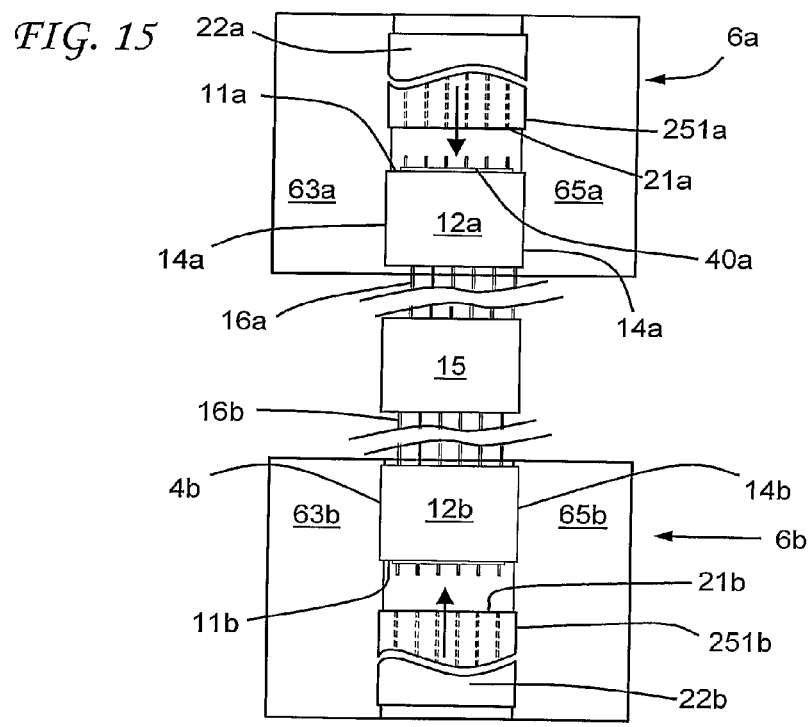

FIGS. 14 and 15 show an assembly which comprises a non-linking substrate 15 each end of which is connected to a connection chip 12a,12b through flexible microfluidic conduits 16a,16b (FIG. 14 shows only one end of the assembly). Each of the connection chips is placed in an alignment jig 6a,6b having flanges 63a,63b and 65a,63b which fit into grooves 141a,141b in sides 14a,14b of the connection chips. Gasket 40a,40b surrounds the ends of the elongate elements 11a,11b protruding from the free ends of the connection chips. Substrate 22a,22b, which has grooves 241a,241b and 251a,251b in its sides, is mounted in the alignment jig, and the chips 12a,12b and 22a,22b are pushed towards each other so that the free ends of the elongate elements enter the corresponding conduits in the substrate and the gasket is compressed to form a fluid-tight junction.

Figure 16:
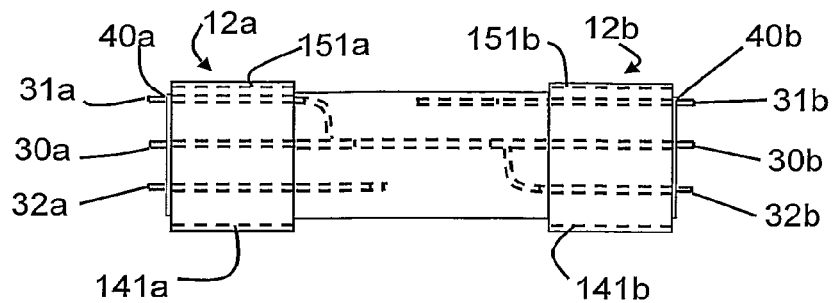
Figure 17:
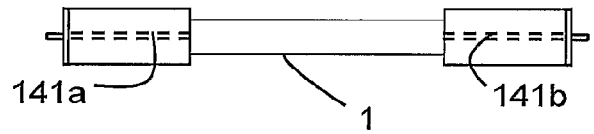

FIGS. 16 and 17 are plan and side views of a chip assembly comprising an active microfluidic chip 17 in which a liquid sample is analyzed or otherwise processed in conduit 261, and connection chips 12a and 12b which are permanently bonded to respective ends of chip 17. The sides of the connection chips include grooves 141a, 151a and 141b, 151b for making repeatable junctions with other substrates (not shown). Optical fibers, electrical leads or other elongate active components 30a and 30b, capillary tubes 31a and 31b and passive elongate components 32a and 32b extend through the connection chips, passing into the chip 17 at one end and protruding at the other end. Gaskets 40a and 40b surround the protruding ends. A chip assembly of this kind is particularly useful when the active microfluidic chip is a non-linking substrate. Further physical protection of the chip 17 can be provided, for example by potting it and the ends of the connection chips in a suitable polymeric material.

Figure 18:
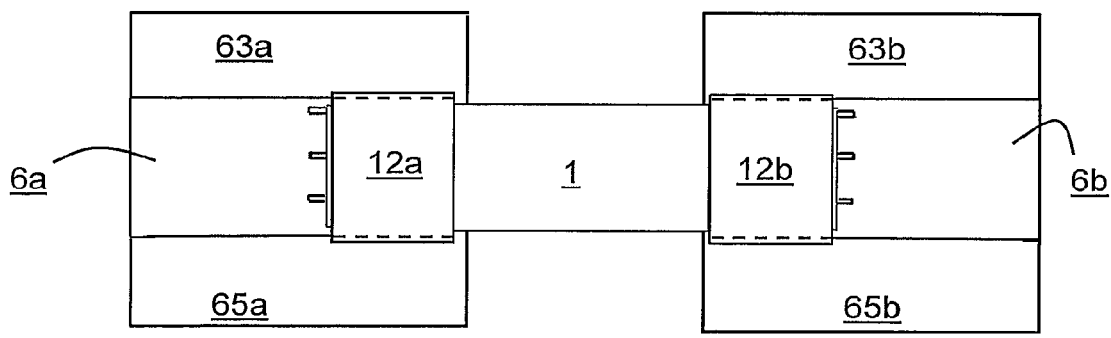
FIG. 18 is a top view of a chip assembly as shown in FIGS. 16 and 17 which also includes alignment jigs.

FIG. 18 is a plan view of a chip assembly as shown in FIGS. 14 and 15 in which each of the connection chips 12a and 12b has been fitted with an alignment jig 6a, 6b having flanges 63a, 65a and 63b, 65b which fit into the grooves of the connection chips.

The invention claimed is:

1. A method of making a liquid-tight junction which comprises:
    providing two substrates, at least one of the substrates having an active elongate component surrounded by a gasket at the interface of the two substrates, and the other substrate being a microfluidic substrate having a microfluidic conduit, each substrate having a pair of alignment features thereon,
    placing the substrates on an alignment jig;

sliding one or both of the substrates along the alignment jig so that the elongate component passes through an interface between the substrates for fluid or signal transmission; and compressing the substrates towards each other by their relative movement, wherein the gasket secures the liquid-tight junction.

2. The method of claim 1, wherein the alignment features on the substrate are grooves corresponding to the alignment jig.

3. The method of claim 1, wherein the active elongated component is a capillary tube.

4. The method of claim 1, wherein the active elongated component is an optical fiber for transmitting an optical signal.

5. The method of claim 1, wherein the active elongate component is a metal conductor for transmitting an electrical signal.

6. The method of claim 1, further comprising at least one passive elongated component.

* * * * *